Figure 1:
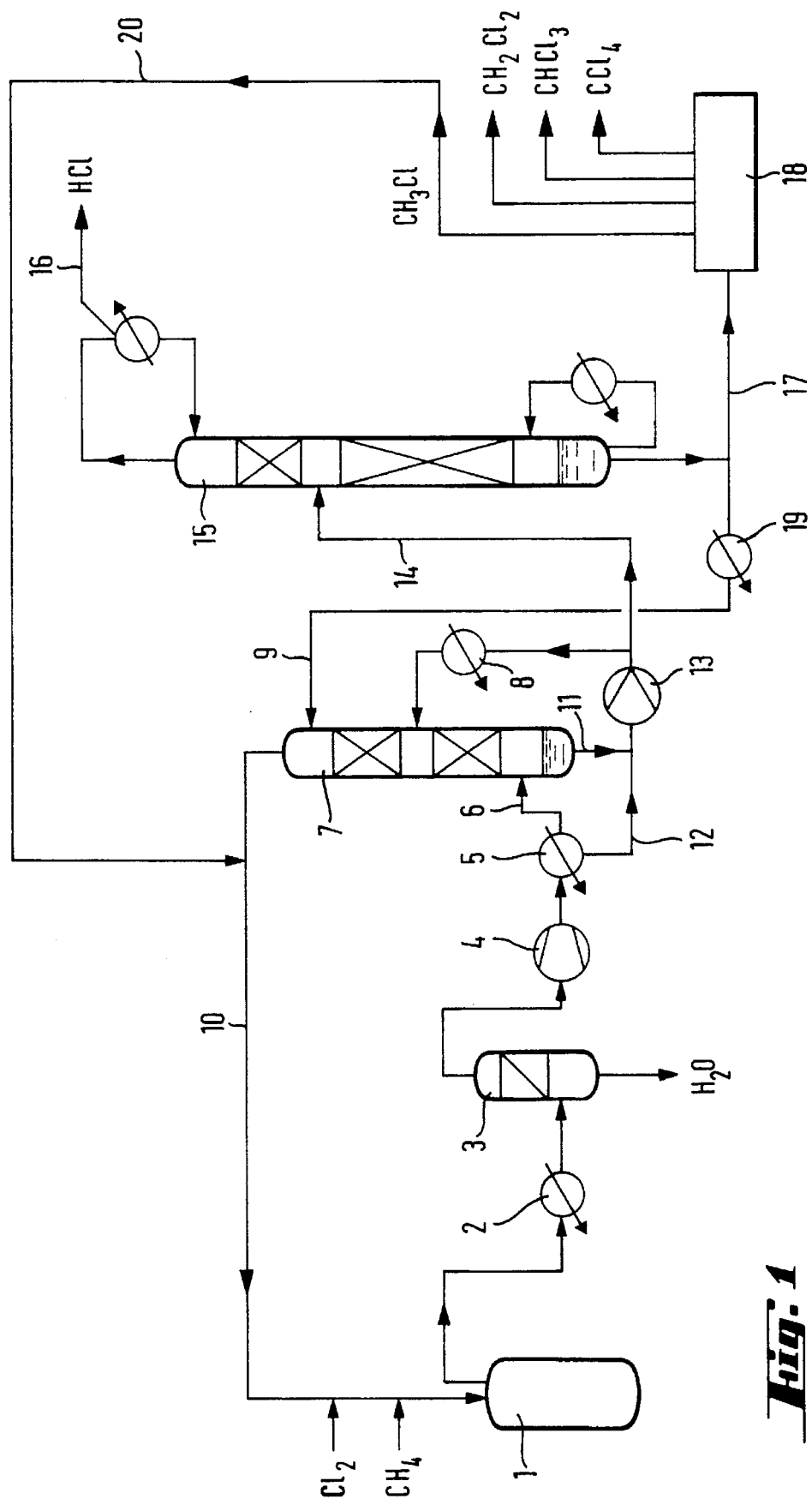

United States Patent [19]
Kraus et al.

[11] Patent Number: 5,611,840
[45] Date of Patent: Mar. 18, 1997

[54] PROCESS FOR SEPARATING OUT HYDROGEN CHLORIDE

[75] Inventors: Werner Kraus, Hünstetten; Thomas Vernaleken, Hofheim; Wolfgang Schick, Frankfurt am Main; Peter M. Roth, Eppstein, all of Germany

[73] Assignee: Hoechst Aktiengesellschaft, Germany

[21] Appl. No.: 564,599

[22] Filed: Nov. 29, 1995

[30] Foreign Application Priority Data

Dec. 1, 1994 [DE] Germany ............... 44 42 743.3

[51] Int. Cl.$^6$ ............... B01D 53/14; B01D 47/06
[52] U.S. Cl. ............ 95/41; 95/42; 95/117; 95/182; 95/233
[58] Field of Search ............... 95/39, 41, 42, 95/117, 178–182, 187, 233

[56] References Cited

U.S. PATENT DOCUMENTS

| | | | |
|---|---|---|---|
| 2,282,712 | 5/1942 | Engs | 95/179 |
| 2,345,696 | 4/1944 | Benning et al. | 95/179 |
| 2,402,978 | 7/1946 | Allen, Jr. et al. | |
| 2,490,454 | 12/1949 | Myers | 95/233 X |
| 2,841,243 | 7/1958 | Hooker et al. | 95/180 |
| 3,097,215 | 7/1963 | Courter et al. | 95/42 X |
| 3,618,295 | 11/1971 | Geiger et al. | 95/182 |
| 3,848,007 | 11/1974 | Foriano | |
| 4,935,220 | 6/1990 | Schneider et al. | 95/42 X |
| 5,000,006 | 3/1991 | Itoh et al. | 95/39 X |
| 5,421,964 | 6/1995 | Mahler et al. | 95/182 X |

FOREIGN PATENT DOCUMENTS

| | | |
|---|---|---|
| 0808699 | 3/1969 | Canada . |
| 2081871 | 12/1971 | France . |
| 1066219 | 4/1967 | United Kingdom . |
| 1172009 | 11/1969 | United Kingdom . |

Primary Examiner—Robert Spitzer
Attorney, Agent, or Firm—Connolly & Hutz

[57] ABSTRACT

The invention relates to a process for separating out hydrogen chloride from a gas mixture forming in the chlorination of methane, which gas mixture contains unreacted methane, its chlorination products and hydrogen chloride formed in the reaction, by cooling and compression of the gas mixture and subsequent scrubbing with a scrubbing liquid which comprises at least one liquid chlorination product of methane. The gas mixture is separated into a methane-containing gas phase and a liquid phase containing hydrogen chloride and methane chlorination products, and the hydrogen chloride is then desorbed from the liquid phase by heating.

8 Claims, 1 Drawing Sheet

PROCESS FOR SEPARATING OUT HYDROGEN CHLORIDE

The invention relates to a process for separating out hydrogen chloride from a gas mixture forming in the chlorination of methane by scrubbing the cooled and compressed mixture with at least one liquid chloromethane.

DE-C 1 568 575 (equivalent to CA Patent 808 699) discloses separating out dry hydrogen chloride from the liquid phase formed in this scrubbing, which liquid phase contains the hydrogen chloride formed in the reaction and the methane chlorination products, by single or multistage rectification.

Surprisingly, it has now been found that the hydrogen chloride can be separated out from the liquid phase much more simply by desorption. The liquid phase freed of hydrogen chloride can then, if desired, be fractionated into the individual chloromethanes by distillation.

The invention relates to a process for separating out hydrogen chloride from a gas mixture forming in the chlorination of methane, which gas mixture contains unreacted methane, its chlorination products and hydrogen chloride formed in the reaction, by cooling and compression of the gas mixture and subsequent scrubbing with a scrubbing liquid which comprises at least one liquid methane chlorination product, by which means the gas mixture is separated into a methane-containing gas phase and a liquid phase containing hydrogen chloride and methane chlorination products, which comprises desorbing the hydrogen chloride from the liquid phase by heating.

Before the scrubbing, the hot gas stream leaving the chlorination reactor is cooled, more precisely preferably to about 20° to 50° C. The gas is then generally dried, for example using a molecular sieve. The gas is then compressed, preferably to a pressure of 7 to 15 bar absolute. It is then cooled again to about 20° to 50° C.

The subsequent scrubbing of the gas mixture in which the methane chlorination products and the hydrogen chloride formed in the chlorination are absorbed together in the scrubbing liquid is generally carried out virtually isothermally, preferably at a pressure of 1 to 35 bar absolute and at a temperature of −50° to +50° C., in particular at a pressure of 7 to 15 bar absolute and at a temperature of 5° to 15° C. This scrubbing is carried out in an absorption column, the scrubbing liquid (one or more liquid chloromethanes) being applied to the top, while the gas mixture flows in countercurrent thereto through the packing bed of the absorption column from bottom to top.

The gas mixture constituents which are not absorbed in the scrubbing, i.e. methane, residual hydrogen chloride, residual chloromethanes and nitrogen, can be recycled to the reactor as circulation gas.

In the lower part of the absorption column, the heat of absorption formed is preferably removed by a circulation pump cooler at a temperature of −20° to +10° C.

The scrubbing liquid laden in the absorption column with hydrogen chloride and the methane chlorination products is passed to a desorber by a pump. The hydrogen chloride is then desorbed alone, while the methane chlorination products remain in the scrubbing liquid. The desorber (desorption column) is generally operated at a pressure of 1 to 35 bar absolute, preferably 10 to 20 bar absolute. The temperature at the top of the desorber is generally −50° to +40° C., preferably −20° to +10° C. The bottom temperature of the desorber is generally 80° to 160° C., preferably 90° to 110° C. The hydrogen chloride is taken off overhead.

The hydrogen-chloride-free chloromethanes are withdrawn at the bottom of the desorber. A portion thereof is reused as scrubbing liquid in the absorption column. The rest can be fractionated by distillation into the individual chloromethanes. If desired, both monochloromethane and dichloromethane can then be recycled to the reactor and further chlorinated. This procedure is chosen if principally trichloromethane is to be prepared. If $CH_3Cl$ and $CH_2Cl_2$ are completely recycled, only the HCl, $CHCl_3$ and $CCl_4$ are obtained as products of the process.

The invention is to be described in more detail by the following example and FIG. 1.

EXAMPLE

For an apparatus as in FIG. 1, the quantities of methane, chlorinated methanes, HCl and $H_2O$ which would be present at positions (6), (9), (10), (11), (12), (14), (16), (17) and (18) of the apparatus were calculated, assuming that the gas mixture characterized below is present in the methane circulation reactor (1) and the resulting $CH_3Cl$ is completely recycled:

In the methane circulation reactor (1) at 420° C. and 3.5 bar absolute the following gas mixture results:

| | |
|---|---|
| $CH_3Cl$: | 43.14 kmol/h |
| $CH_2Cl_2$: | 18.08 kmol/h |
| $CHCl_3$: | 12.60 kmol/h |
| $CCl_4$: | 1.04 kmol/h |
| $CH_4$: | 211.12 kmol/h |
| HCl: | 371.22 kmol/h |
| $H_2O$: | 0.14 kmol/h |

This mixture is passed into cooler (2). After the gas has been cooled to approximately 30° C., it is passed into vessel (3) via a molecular sieve (silica gel) to separate out the water. The gas is then compressed in the compressor (4) to 7 bar absolute and then again cooled to 30° C. in cooler (5). The portion of the starting gas which is not condensed in the cooling is fed via line (6) to the absorption column (7). This is likewise under a pressure of 7 bar absolute and is operated at about 0° C. by a circulation pump cooler (8). At the top of column (7), a mixture of chloromethanes is fed in as scrubbing liquid via line (9) at a temperature of −20° C.

The constituents of the starting gas which are not absorbed in column (7):

| | |
|---|---|
| $CH_3Cl$: | 23.94 kmol/h |
| $CH_2Cl_2$: | 2.37 kmol/h |
| $CHCl_3$: | 0.66 kmol/h |
| $CCl_4$: | 0.03 kmol/h |
| $CH_4$: | 206.47 kmol/h |
| HCl: | 282.04 kmol/h | leave the column (7) overhead and are recycled to reactor (1) via line (10).

The bottom efflux of column (7), comprising

| | |
|---|---|
| $CH_3Cl$: | 50.64 kmol/h |
| $CH_2Cl_2$: | 37.89 kmol/h |
| $CHCl_3$: | 26.57 kmol/h |
| $CCl_4$: | 2.13 kmol/h |
| $CH_4$: | 4.36 kmol/h |
| HCl: | 86.16 kmol/h | is taken off via line (11) and is returned to the desorber (15) via pump (13) and line (14) together with the portion of starting gas condensed in cooler (5) and withdrawn via line (12). At the top of the desorber, gaseous hydrogen chloride is withdrawn at −20° C. and 15 bar absolute via line (16). Some of the hydrogen-chloride-free bottom efflux (approximately 100° C., 15.1 bar absolute) of the desorber (15) is fed via line (17) to the distillation unit (18). Here, the mixture of chloromethanes is fractionated in a plurality of rectifying columns to give

| | |
|---|---|
| $CH_3Cl$: | 43.12 kmol/h |
| $CH_2Cl_2$: | 18.08 kmol/h |
| $CHCl_3$: | 12.60 kmol/h |
| $CCl_4$: | 1.04 kmol/h |

The portion of the bottom efflux of the desorber (15) which is not fed to the distillation is passed via cooler (19) and line (9) to the absorption column (7) and fed therein as scrubbing liquid at the top.

The $CH_3Cl$ is recycled to the reactor (1) via the lines (20) and (10).

The table below shows the amounts of the individual components assumed to be at the exit of the methane circulation reactor (1) and the calculated amounts at the other positions mentioned above.

TABLE

| | Quantitative balance [kmol/h] | | | | | | | | | |
|---|---|---|---|---|---|---|---|---|---|---|
| | Exit of (1) | (6) | (9) | (10) | (11) | (12) | (14) | (16) | (17) | Exit of (18) |
| $CH_3Cl$ | 43.14 | 40.41 | 34.17 | 23.94 | 50.64 | 2.73 | 53.37 | 0.33 | 18.87 | 43.12 |
| $CH_2Cl_2$ | 18.08 | 11.81 | 28.45 | 2.37 | 37.89 | 6.27 | 44.16 | — | 15.71 | 18.08 |
| $CHCl_3$ | 12.60 | 5.64 | 21.59 | 0.66 | 26.57 | 6.96 | 33.53 | — | 11.94 | 12.60 |
| $CCl_4$ | 1.04 | 0.34 | 1.82 | 0.03 | 2.13 | 0.70 | 2.83 | — | 1.01 | 1.04 |
| $CH_4$ | 211.12 | 210.83 | — | 206.47 | 4.36 | 0.29 | 4.65 | 4.65 | — | — |
| HCl | 371.72 | 368.20 | — | 282.04 | 86.16 | 3.02 | 89.18 | 89.18 | — | — |
| $H_2O$ | 0.14 | — | — | — | — | — | — | — | — | — |

We claim:

1. A process for separating out hydrogen chloride from a gas mixture forming in the chlorination of methane, which gas mixture contains unreacted methane, its chlorination products and hydrogen chloride, by cooling and compression of the gas mixture and subsequent scrubbing with a scrubbing liquid which comprises at least one liquid methane chlorination product, and wherein the gas mixture is separated into a methane-containing gas phase and a liquid phase containing hydrogen chloride and methane chlorination products, and desorbing the hydrogen chloride from the liquid phase by heating.

2. The process as claimed in claim 1, wherein the gas mixture is cooled to 20° to 50° C. before the scrubbing.

3. The process as claimed in claim 1, wherein the gas mixture is dried before the scrubbing.

4. The process as claimed in claim 1, wherein the gas mixture is compressed before the scrubbing to a pressure of 7 to 15 bar absolute.

5. The process as claimed in claim 1, wherein the scrubbing is carried out at a pressure of 1 to 35 bar absolute and at a temperature of −50° to +50° C.

6. The process as claimed in claim 1, wherein the scrubbing is carried out at a pressure of 7 to 15 bar absolute and at a temperature of 5° to 15° C.

7. The process as claimed in claim 1, wherein desorbing the hydrogen chloride is performed in a desorber having a top and bottom at a pressure of 1 to 35 bar absolute and at a temperature of −50° to +40° C. at the top of the desorber and at a temperature of 80° to 160° C. at the bottom of the desorber.

8. The process as claimed in claim 1, wherein desorbing the hydrogen chloride is performed in a desorber having a top and a bottom at a pressure of 10 to 20 bar absolute and at a temperature of −20° to +10° C. at the top of the desorber and at a temperature of 90° to 110° C. at the bottom of the desorber.

* * * * *